US008958076B2

(12) United States Patent
Takahashi et al.

(10) Patent No.: US 8,958,076 B2
(45) Date of Patent: Feb. 17, 2015

(54) SURFACE SHAPE MEASURING APPARATUS

(75) Inventors: Kazuo Takahashi, Naka-gun (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 41 days.

(21) Appl. No.: 13/993,630

(22) PCT Filed: Nov. 30, 2011

(86) PCT No.: PCT/JP2011/006671
§ 371 (c)(1),
(2), (4) Date: Jul. 15, 2013

(87) PCT Pub. No.: WO2012/090392
PCT Pub. Date: Jul. 5, 2012

(65) Prior Publication Data
US 2013/0278926 A1    Oct. 24, 2013

(30) Foreign Application Priority Data
Dec. 27, 2010    (JP) ................................ 2010-289103

(51) Int. Cl.
*G01B 11/30*    (2006.01)
*G01N 21/95*    (2006.01)
(Continued)

(52) U.S. Cl.
CPC .......... *G01N 21/9501* (2013.01); *G01B 11/303* (2013.01); *G01N 21/94* (2013.01); *H01L 22/12* (2013.01)
USPC .......................................................... 356/600

(58) Field of Classification Search
USPC ...................................... 356/600; 250/559.22
See application file for complete search history.

(56) References Cited

U.S. PATENT DOCUMENTS 5,428,442 A    6/1995    Lin et al.
7,286,218 B2    10/2007    Tiemeyer et al.
(Continued)

FOREIGN PATENT DOCUMENTS

JP    63-143830 A    6/1988
JP    4-194738 A    7/1992
(Continued)

OTHER PUBLICATIONS

Corresponding International Search Report with English Translation dated Mar. 6, 2012 (five (5) pages).

*Primary Examiner* — Roy M Punnoose
(74) *Attorney, Agent, or Firm* — Crowell & Moring LLP

(57) ABSTRACT

Surface states have traditionally been measured with apparatuses such as an atomic force microscope (AFM), and these measurements have been high in resolution but low in speed. In conventional apparatuses for inspecting the foreign matter sticking to a wafer surface, and for inspecting defects present on the wafer surface, the inspection has had a tendency to be restricted in a region of the highest noise level arising from the roughness of the surface, the surface state, and/or crystal orientations, and thereby to reduce detection sensitivity in a region of lower noise levels. In these conventional techniques, signal processing of the light scattered from the object to be inspected has been based only upon the intensity of the light. This invention acquires three-dimensional data by, during such signal processing, adding detection intervals and the frequency of detection, as well as the intensity of light. The invention measures surface roughness of a target object (wafer) by creating region-specific three-dimensional maps from the three-dimensional data, then estimating the surface state of the wafer from analytical results, processing this estimated surface state as physical quantities, and analyzing the data.

4 Claims, 12 Drawing Sheets

(51) Int. Cl.
*G01N 21/94* (2006.01)
*H01L 21/66* (2006.01)

(56) References Cited

U.S. PATENT DOCUMENTS

| | | | |
|---|---|---|---|
| 7,755,751 B2 | 7/2010 | Matsui | |
| 7,884,948 B2 | 2/2011 | Miyoshi et al. | |
| 8,101,935 B2 | 1/2012 | Takahashi et al. | |
| 8,189,205 B2 | 5/2012 | Miyoshi et al. | |
| 8,265,375 B2 * | 9/2012 | Shirley | 382/154 |
| 2008/0111996 A1 * | 5/2008 | Takeda et al. | 356/511 |

| | | | |
|---|---|---|---|
| 2012/0019835 A1 | 1/2012 | Nakao et al. | |

FOREIGN PATENT DOCUMENTS

| | | |
|---|---|---|
| JP | 7-243977 A | 9/1995 |
| JP | 2003-7681 A | 1/2003 |
| JP | 2003-240723 A | 8/2003 |
| JP | 2004-61447 A | 2/2004 |
| JP | 2006-64496 A | 3/2006 |
| JP | 2009-133778 A | 6/2009 |
| JP | 2009-168672 A | 7/2009 |
| JP | 2010-197352 A | 9/2010 |
| WO | WO 2012090392 A1 * | 7/2012 |

* cited by examiner

SURFACE SHAPE MEASURING APPARATUS

TECHNICAL FIELD

The present invention relates to a surface shape measuring apparatus and method for obtaining a surface state of an object to be inspected, the invention further relating to an apparatus and method for inspecting defects present on the surface of the object.

For example, the present invention is directed to an apparatus and method for measuring surface roughness of a semiconductor wafer in semiconductor device manufacturing processes, and to an apparatus and method for inspecting defects and the like present on the surface of the semiconductor wafer.

BACKGROUND ART

In manufacturing processes for a semiconductor device, patterns are transferred onto the surface of a bare wafer and then unnecessary sections of the wafer are removed by etching to form electrical circuits. In the semiconductor device manufacturing processes used to form the circuits, foreign substances sticking to the surface of the wafer, defects present on the wafer surface, and the like are major causative factors in the deterioration of a production yield.

Foreign substances sticking to the wafer surface, and defects present on the wafer surface are managed in each manufacturing process, and a surface inspection apparatus detects these foreign substances and defects at high sensitivity and high throughput. In the surface inspection apparatus, the surface state (e.g., surface roughness) of the object under measurement is another crucial factor governing the photolithographic performance of the manufacturing apparatus. During the surface inspection, the surface state of the wafer is also an important factor relating to detection sensitivity, and thus has a substantial need for measurement.

Examples of conventional apparatuses and techniques for inspecting defects and/or measuring surface states are seen in Patent Documents 1 to 7 listed below.

PRIOR ART LITERATURE

Patent Documents

Patent Document 1: JP-1988-143830-A
Patent Document 2: JP-2004-061447-A
Patent Document 3: JP-1995-243977-A
Patent Document 4: JP-2003-007681-A
Patent Document 5: U.S. Pat. No. 7,286,218
Patent Document 6: U.S. Pat. No. 5,428,442
Patent Document 7: U.S. Pat. No. 7,755,751

SUMMARY OF THE INVENTION

Problems to be Solved by the Invention

Surface states have traditionally been measured with apparatuses such as an atomic force microscope (AFM), and these measurements have been performed on a point-by-point basis by scanning a high-resolution high-sensitivity sensor, one for one, at low speed and high resolution. This has entailed too much measuring time to inspect the entire region of the object under measurement or to inspect a large number of samples. Briefly, in these conventional techniques, attention has not been given to rapidly obtaining highly accurate information on the surface state of the substrate over a relatively wide range of the substrate surface.

In conventional techniques relating to defect inspection, inspection threshold levels have been set according to the magnitude of the light scattered from the object to be inspected, and it has been common to set the same threshold levels for the entire surface of the target object. The surface states of actual objects to be inspected, however, are not uniform and if the same threshold levels are set for the entire surface of the target object, the inspection may be restricted in a region of the highest noise level resulting from the roughness of the surface, the surface state, and/or crystal orientations, and is likely to reduce detection sensitivity in a region of lower noise levels. This likelihood has not received attention in the conventional techniques.

Means for Solving the Problems

The present invention focuses upon the intervals of a detection signal that have not caught attention in the foregoing conventional techniques.

In the conventional techniques, the signal processing of inspection object-scattered light that is one of the methods of inspecting the foreign substances and defects existing on a wafer has been based only upon the intensity of the light. In contrast to this, the present invention implements signal processing with three-dimensional data by, for example, acquiring detection intervals and the frequency of detection in addition to the intensity of light by use of a high-speed sampling device.

The present invention measures surface roughness of an object (wafer) under inspection by, for example, creating region-specific three-dimensional maps from the three-dimensional data, then estimating the surface state of the wafer from analytical results, processing this estimated surface state as physical quantities, and analyzing the data.

The present invention improves defect and foreign substance detection performance by, for example, creating the above three-dimensional data for each region of the object under measurement, next adding threshold levels to the three-dimensional data, and setting the three-dimensional threshold levels for each region.

The present invention includes, for example, a plurality of spatially independent detectors and conducts three-dimensional simultaneous defect determinations upon detection signals to detect and analyze any defects having orientation features on the surface of the object being inspected.

Effects of the Invention

The present invention yields the following advantageous effects. These effects may each be yielded independently or may all be yielded at the same time:

(1) In accordance with the invention, the surface state of the substrate can be analyzed more closely than in the conventional techniques.

(2) In accordance with the invention, more accurate defect inspection than in the conventional techniques can be achieved.

More specifically, it can be expressed that the present invention yields the following advantageous effects:

(3) In accordance with the invention, since surface roughness measurement, as opposed to conventional point-by-point low-speed scanning, uses high-speed scanning under the illumination light determined in an illumination system, the time required for surface roughness measurement is significantly shortened and the number of samples measured can therefore be increased, which contributes to improving semiconductor device-manufacturing process efficiency.

(4) Although the conventional inspection based on uniform inspection threshold levels has suffered the deterioration of detection sensitivity due to the restrictions associated with the noise arising from the surface roughness, surface state, and/or crystal orientations of the target object, three-dimensional defect determination allows the above causes of fluctuations in detection sensitivity to be classified according to situation, and thus, detection sensitivity to be maximized.

(5) Three-dimensional simultaneous defect determination of detection signals by the plurality of spatially independent detectors allows improvement of accuracy in the detection of the defects having orientation features on the surface of the target object, and efficient analysis and classification of the orientation features.

MODE FOR CARRYING OUT THE INVENTION

Hereunder, embodiments of the present invention will be described using the accompanying drawings. However, apparatus configurations and methods according to the present invention are not limited to those shown in the relevant drawings, and may be modified into various forms without departing from the scope of its technical philosophy.

(First Embodiment)

Figure 1:
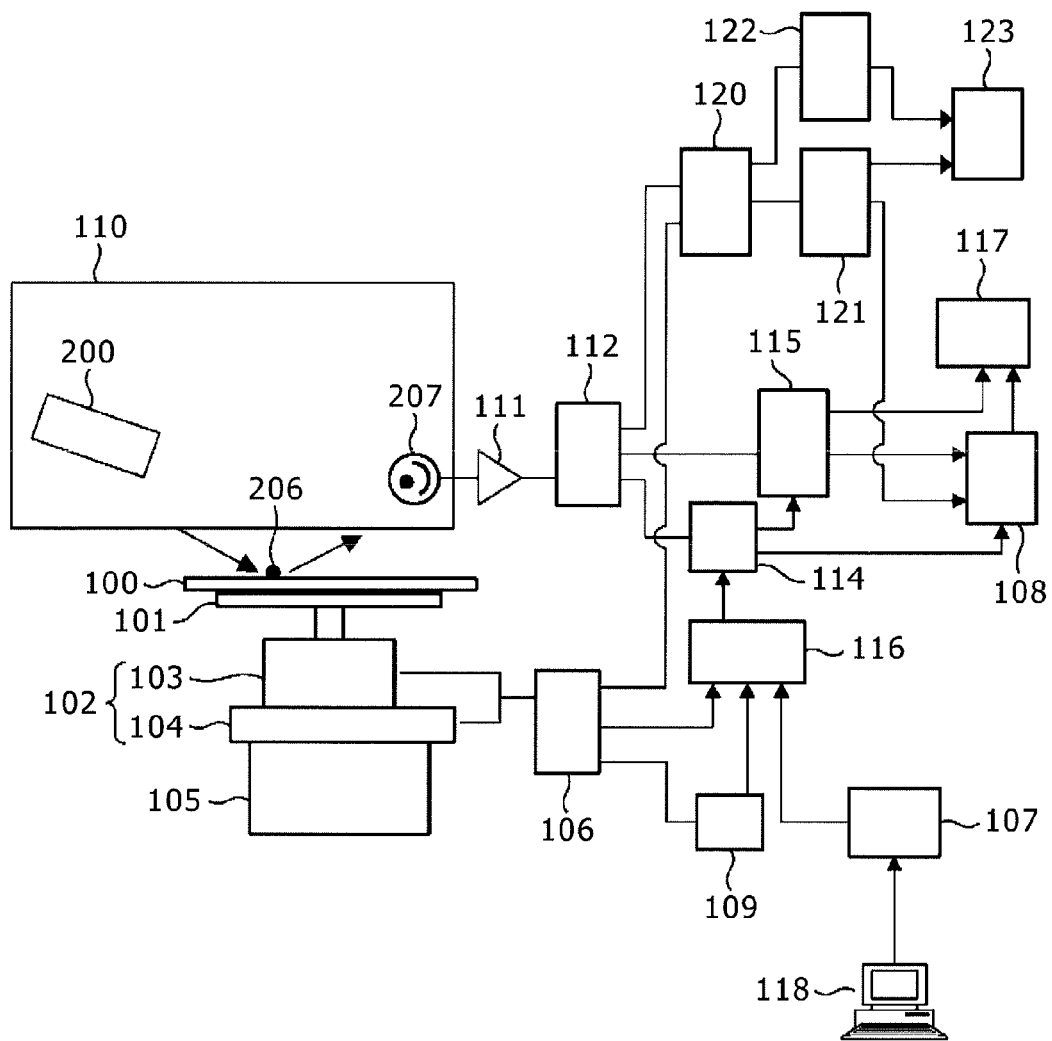
FIG. 1 is a diagram showing a schematic configuration of a first embodiment.

An inspection apparatus according to a first embodiment of the present invention is shown in FIG. 1.

A semiconductor wafer 100, an object to be inspected, is vacuum-held by a chuck 101. The chuck 101 is mounted on a target object moving stage 102 consisting of a rotating stage 103 and a translating stage 104, the moving stage 102 being mounted on a Z-stage 105. The rotating stage 103 undertakes θ-rotational moving, and the translating stage 104 undertakes translational R-moving.

Figure 2:
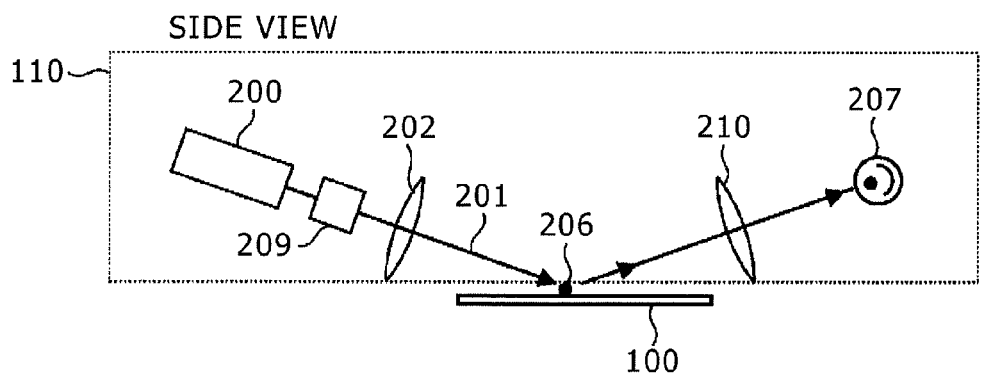
FIG. 2 is a side view showing an illumination and detection optical system in the first embodiment.
Figure 3:
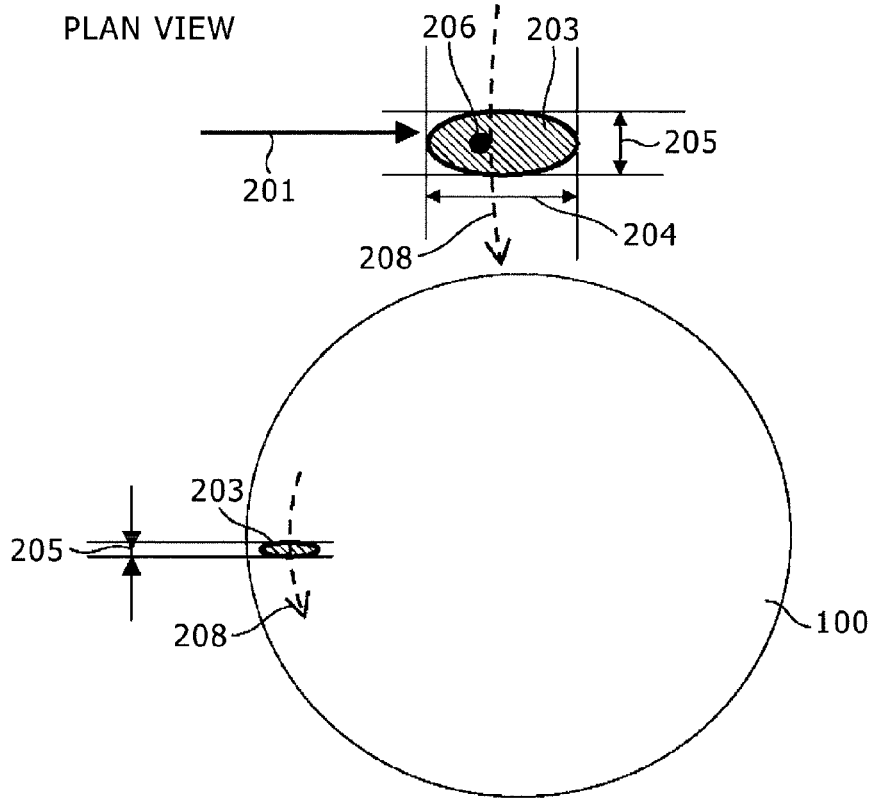
FIG. 3 is a plan view showing an illumination spot in the first embodiment.

FIG. 2 is a side view showing an illumination and detection optical system 110 disposed above the semiconductor wafer 100. FIG. 3 is a plan view illustrating an illumination spot formed on the semiconductor wafer 100.

A laser light source is used as an illumination light source 200. A beam of light 201 that has been emitted from the light source 200 enters an expander 209 and an irradiation lens 202, thereby forming the illumination spot 203 of a predefined size. The illumination light is, for example, P-polarized light. The illumination and detection optical system 110 is constructed to conduct off-axis (oblique) incident illumination. That is to say, the illumination light strikes the surface of the semiconductor wafer 100, the target object, at substantially a Brewster's angle with respect to crystal silicon (Si). This is why the illumination spot 203 has substantially an elliptical shape as shown in the plan view of FIG. 3. The inside of a border line where illuminance decreases to 'one over the second power of "e"' (where "e" is the base of a natural logarithm) of a central portion of the illumination spot is newly defined as the illumination spot 203 here.

Width 204 of the illumination spot 203 in a direction of its major axis is defined as d1, and width 205 in a direction of its minor axis, as d2. The illumination spot 203 is scanned in a θ-direction 208 as denoted by a dotted line marked with an arrow in FIG. 3.

The target object moving stage 102 helically scans the illumination spot 203 in relative fashion on substantially the entire surface of the semiconductor wafer 100 by varying a θ-rotational moving action and a translational R-moving action in combination with time.

A converging lens 210 is constructed so that it can converge scattered light at a low angle of elevation to efficiently capture the light scattered by a foreign substance small enough to follow Rayleigh scattering. In this construction, the scattered light from the foreign substance/defect 206 is passed through the converging lens 210 and detected by a photodetector 207.

A light-scattering optical signal is obtained from the photodetector 207. A photodiode, a high-speed optical conversion device, is used as the photodetector 207 in the present embodiment. This photodiode, while desirably being such a rapidly responsive device as an avalanche photodiode, may be a photodetector based on other principles of detection, only if the photodetector can detect with high sensitivity and at high speed the light scattered from the foreign substance.

Figure 4:
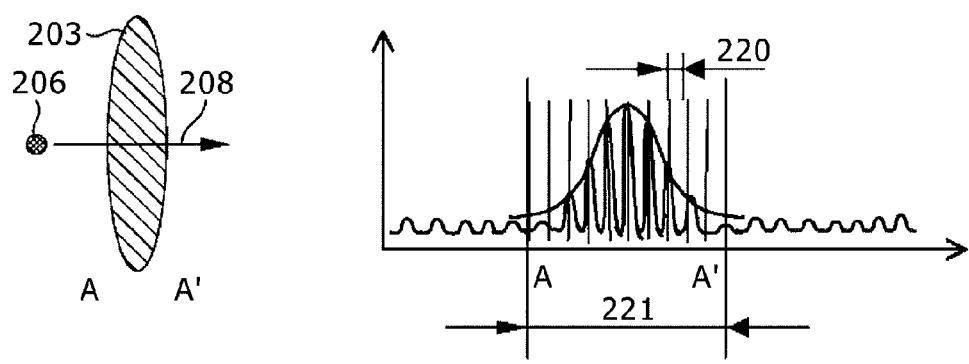
FIG. 4 is a diagram that shows sampling.

Next, signal processing in the present embodiment is described below. The scattered light signal from the photodetector 207 is amplified by an amplifier 111, then sampled at predefined sampling intervals ΔT220 by an A/D converter 112, and converted into digital data by the converter. The sampling intervals ΔT220 are determined so that a signal waveform shown in FIG. 4 can be sampled with sufficient time resolution. For example, if half-width at the outermost circumferential edge of the ellipse in FIG. 4 is expressed as minimal signal waveform width ΔSout221, then it follows that ΔT=Sout÷10. This sampling produces a group of time-series digital data corresponding to the signal waveform shown in FIG. 4.

A variable filtering process 114 is conducted as an example of digital filtering upon the digital data from the A/D converter 112, and after creation of the data of low-frequency components only, subtraction from the data obtained from the A/D converter 112 occurs inside a subtractor 115, whereby the difference obtained becomes information only on intensity of the scattered light that corresponds to dimensions of the foreign substance/defect.

A frequency band used in the variable filtering process 114 is controlled by an arithmetic unit 116, the control being based on information relating to a rotating speed of the target object moving stage, a coordinate position obtained in the scanning direction by coordinate detection means, and a size of the illumination spot. Calculation parameters used in the arithmetic unit are based on information from an inspection coordinate detection mechanism 106 and a host CPU 107.

The intensity value of the scattered light that has been obtained as a result of above data processing is compared with a predefined detection threshold value (described in detail later herein) by a foreign substance/defect determination mechanism 108, and if the intensity value of the scattered light is equal to or greater than the threshold value, the defect determination mechanism 108 generates defect determination information.

Upon the generation of the defect determination information, a defect coordinate detection mechanism 109 calculates the coordinate position of the detected foreign substance/defect from the information received from the inspection coordinate detection mechanism 106.

In addition, a particle size calculation mechanism 117 calculates the dimensions of the detected foreign substance/defect from the intensity value of the scattered light.

The rotating speed of the target object moving stage and the size of the illumination spot are set by a user via input means 118 and operated on inside the inspection apparatus.

The input means 118 may be a keyboard or a pointing device such as a mouse. Additionally, an independent memory with the above necessary information stored therein may be input to the inspection apparatus via an interface not shown.

Next, measurement of the surface state in the present embodiment is described below.

Prior to the measurement of the surface state, the time-series digital data group that the A/D converter 112 has sampled at the sampling intervals ΔT220 is first saved in a measured-data memory 120. The time-series digital data group, together with coordinate positions on the surface under inspection, is addressed and saved at sampling interval clock cycles (detection intervals).

Figure 5:
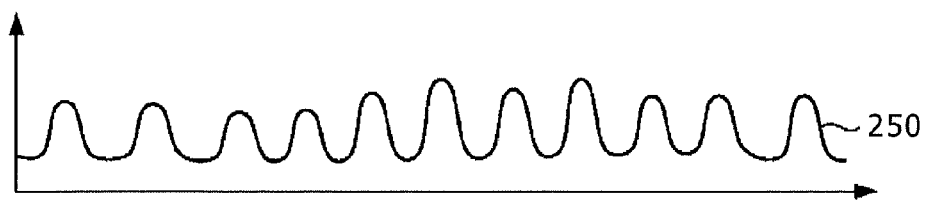
FIG. 5 shows a sampling signal waveform obtained from a sample narrow in roughness pitch and small in the amount of roughness.

Next, a 3D analyzing mechanism 121 creates data of FIG. 5 from the signal intensity, signal intensity detection intervals, and signal intensity detection rate (frequency of detection) contained in the time-series digital data group. The creation of the data shown in FIG. 5 can be expressed as, for example in the present embodiment, converting the sampled data into three-dimensional data based on the signal intensity, the detection intervals, and the frequency of detection, and using three-dimensional conversion results to obtain information on the surface shape of the wafer (substrate).

Figure 22:
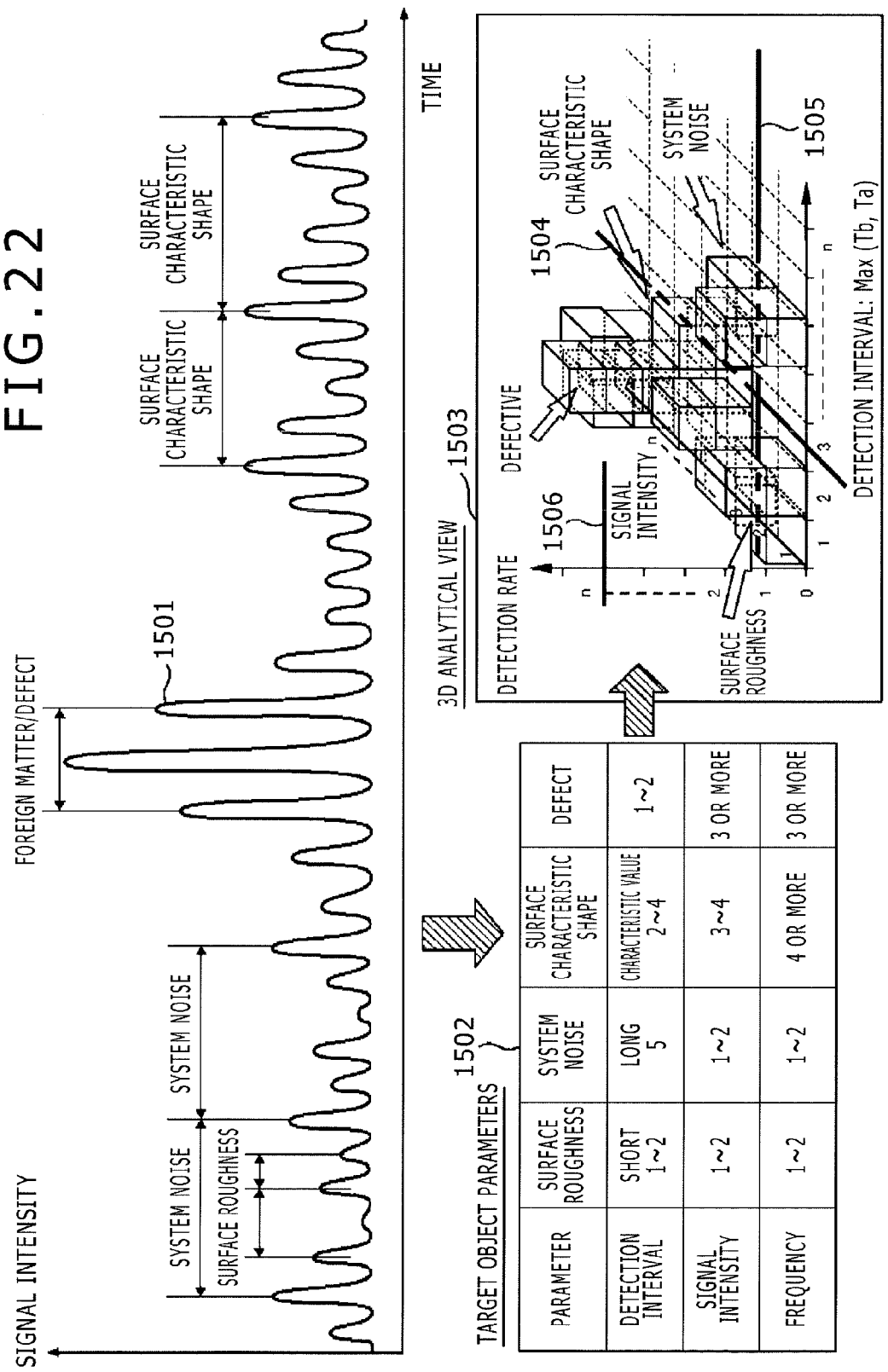
FIG. 22 is a diagram that illustrates surface shape measurement in the first embodiment.

Further details of this are described below. In the present embodiment, as shown in FIG. 22, parameters 1502 are provided for each measurement region and the time-series digital data group 1501 is used to classify the shape of the surface on the basis of the parameters 1502. Three-dimensional measurement results 1503 are an example of classification. Additionally in the present embodiment, since these classification results automatically indicate that the shape of the surface has been classified, highly accurate inspection takes place with a first threshold value 1504, second threshold value 1505, and third threshold value 1506 provided for each of the signal intensity, the detection intervals, and the frequency of detection. This is expressed by the fact that the 3D analyzing mechanism 121 and the defect determination mechanism 108 are connected via a signal line 124.

In other words, the present embodiment is based on the following concept. the shape of the substrate surface is likely to differ according to characteristics or reason of the shape, such as surface roughness, system noise, surface characteristic shape (a characteristic stepped shape in an epitaxially grown wafer), and/or geometry of the defect. When viewed in a perspective of signal intensity, signal intensity detection intervals, and the frequency of detection, therefore, the shape of the substrate surface will correspondingly exhibit a characteristic behavior. Capturing this characteristic behavior will enable further detailed analysis of the surface, and the analytical results obtained will also be applicable to the defect inspection.

Figure 23:
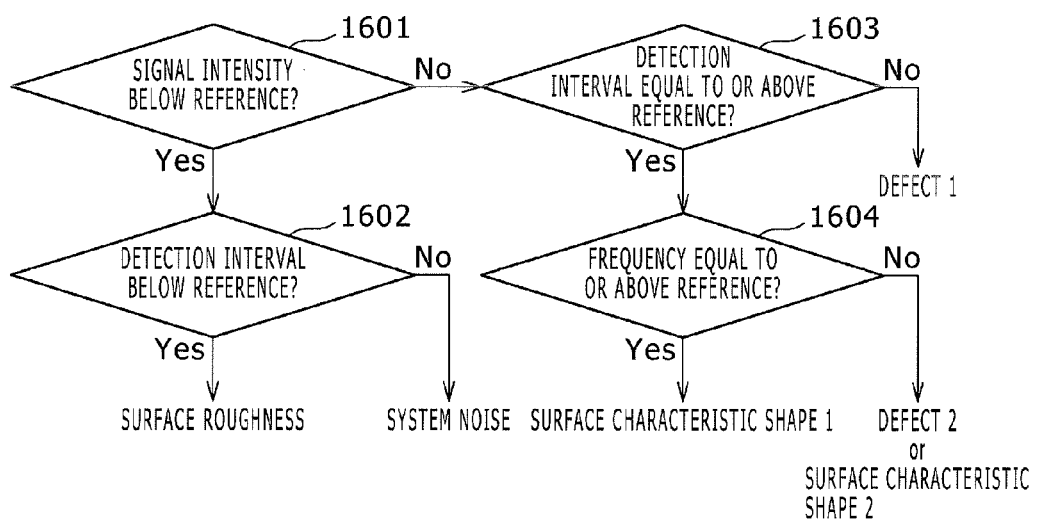
FIG. 23 is a flow diagram of surface analysis by a 3D analyzing mechanism 121 in the first embodiment.

FIG. 23 implies that after it has been simply determined whether the values of the above determination factors are equal to or above respective reference values or below the respective reference values, the signal detected may vary to a certain extent, even when the shape of the substrate surface is of the same kind. Accordingly, a certain degree of spread may be assigned to each reference. That is to say, signal intensity, the signal intensity detection intervals, and the frequency of detection may be determined whether they lie within certain ranges or overstep the ranges.

Next, a flow of the surface analysis by the 3D analyzing mechanism 121 is described below using FIG. 23. In the present embodiment, attention is first focused upon signal intensity and only signal intensity data equal to or smaller than the reference is extracted from the time-series digital data group 1501 (step 1601). If any signal intensity data equal to or smaller than the reference is determined to exist, attention is next focused upon the detection intervals corresponding to the particular signal intensity data. In step 1602, if the detection intervals are equal to or smaller than the reference, the signal is determined to represent the roughness of the surface, or if the detection intervals are above the reference, the signal is determined to represent system noise.

Conversely, if the detected signal is determined in step S1601 to be above the reference, attention is, next focused upon the detection intervals, for determination. In step 1602, if the detection intervals are equal to or smaller than the reference, the signal is determined to represent a defect 1, or if the detection intervals are below the reference, control proceeds to step 1604. If the detection intervals of the detected signal are above the reference, the frequency of detection is determined whether it is above the relevant reference. If the frequency of detection is above the reference, the signal is determined to represent a surface characteristic shape 1, or if the frequency of detection is equal to or less than the reference, the signal is determined to represent a defect 2 other than the defect 1, or a surface characteristic shape 2 other than the surface characteristic shape 1.

Hereinafter, the present embodiment will be described using further detailed cases. The surface state of the semiconductor wafer 100 is classified into one of such patterns as in FIGS. 5 to 8, depending on a pitch of surface roughness and the amount of roughness (particle size). In association with this pattern, the three-dimensional data obtained appears as one of such patterns as in FIGS. 10 to 13. In a case of a 32-nm semiconductor-manufacturing process generation node, reference values for the roughness pitch and amount of roughness of the surface under inspection are expressed as 0.100 ppm in RMS (root mean square) roughness.

Figure 10:
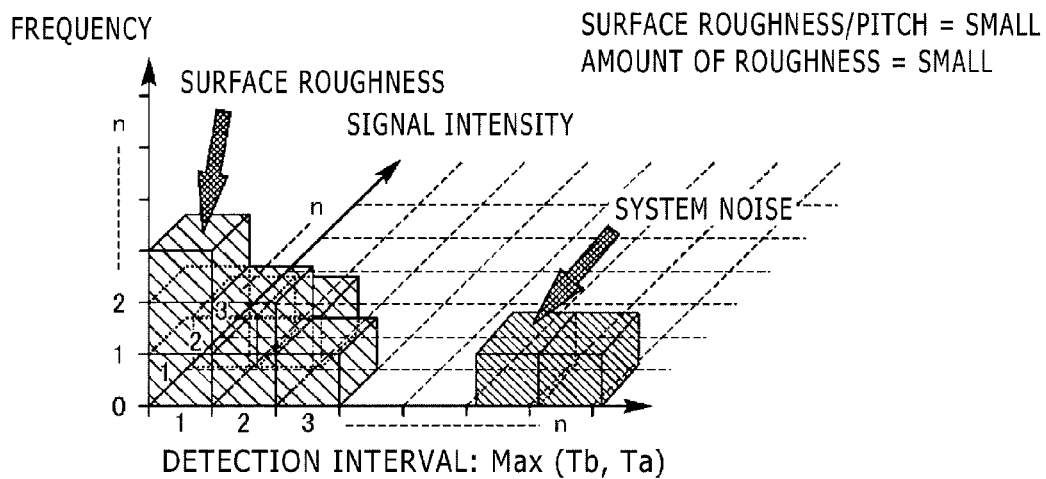
FIG. 10 shows a 3D graphic pattern denoting a sample narrow in roughness pitch and small in the amount of roughness.

When the surface under inspection is narrow in roughness pitch and small in the amount of roughness as shown in FIG. 5, the signal pattern appears as shown in FIG. 10.

Figure 6:
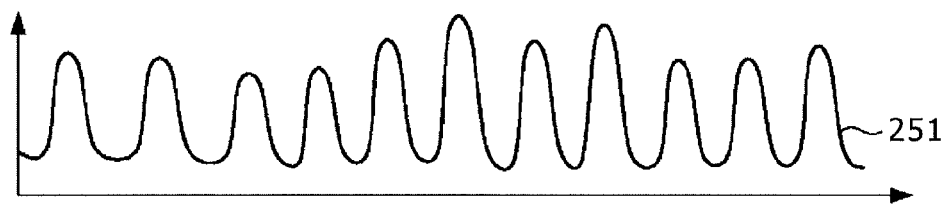
FIG. 6 shows a sampling signal waveform obtained from a sample narrow in roughness pitch and large in the amount of roughness.
Figure 11:
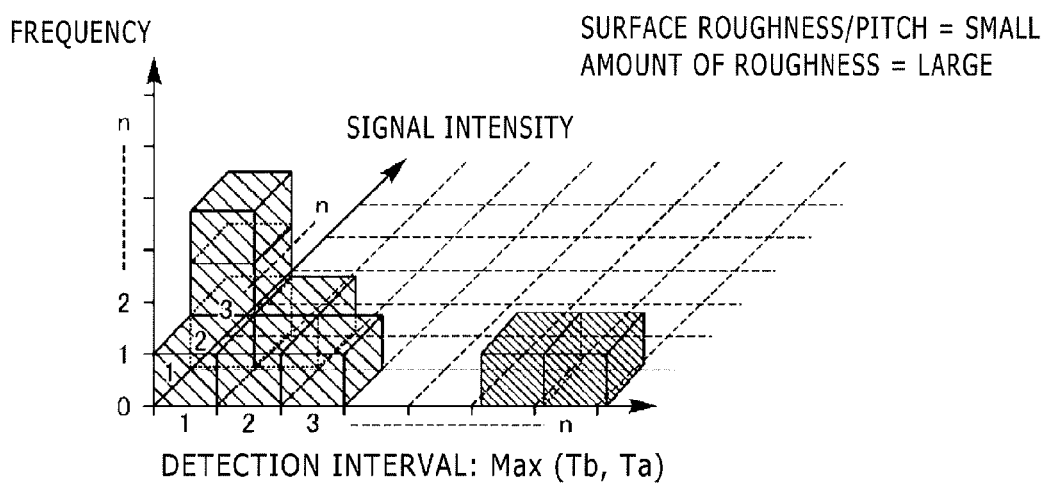
FIG. 11 shows a 3D graphic pattern denoting a sample narrow in roughness pitch and large in the amount of roughness.

When the surface under inspection is narrow in roughness pitch and large in the amount of roughness as shown in FIG. 6, the signal pattern appears as shown in FIG. 11.

Figure 7:
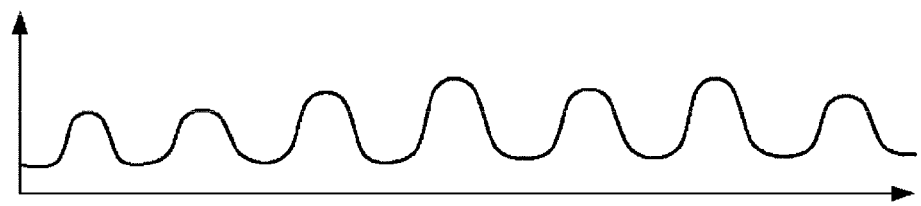
FIG. 7 shows a sampling signal waveform obtained from a sample wide in roughness pitch and small in the amount of roughness.
Figure 12:
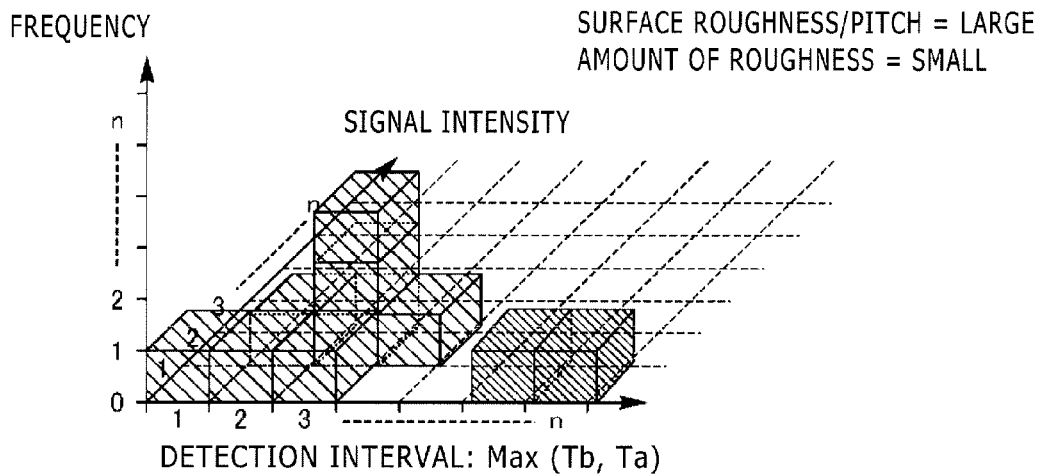
FIG. 12 shows a 3D graphic pattern denoting a sample wide in roughness pitch and small in the amount of roughness.

When the surface under inspection is wide in roughness pitch and small in the amount of roughness as shown in FIG. 7, the signal pattern appears as shown in FIG. 12.

Figure 8:
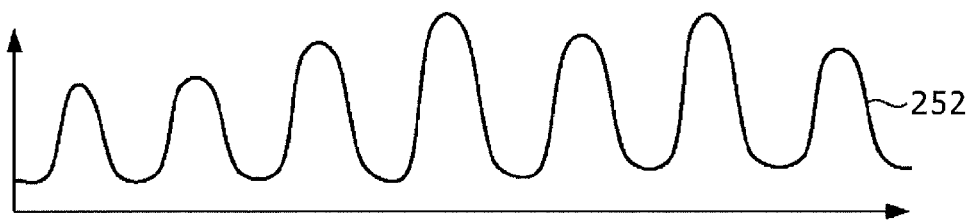
FIG. 8 shows a sampling signal waveform obtained from a sample wide in roughness pitch and large in the amount of roughness.
Figure 13:
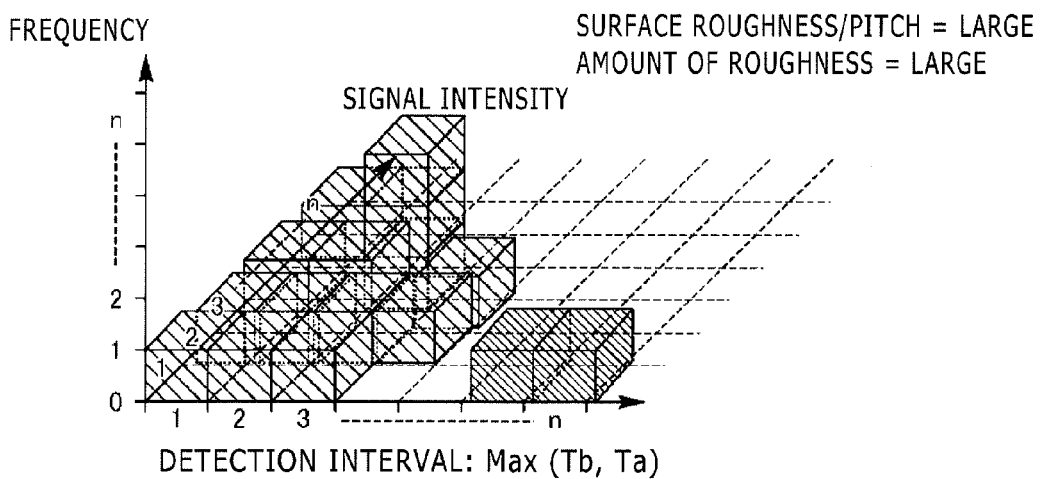
FIG. 13 shows a 3D graphic pattern denoting a sample wide in roughness pitch and large in the amount of roughness.

When the surface under inspection is wide in roughness pitch and large in the amount of roughness as shown in FIG. 8, the signal pattern appears as shown in FIG. 13.

The determination of surface roughness is first described here. Substantially the same pattern as in one of FIGS. 5 to 8 is analyzed using an external measuring apparatus such as an AFM, and thereby, physical quantities are obtained as surface roughness information. In the present embodiment, the surface roughness information is stored within a surface roughness determination mechanism 123. Next, substantially the same pattern as in one of FIGS. 5 to 8 is analyzed using the inspection apparatus of the present embodiment, and thereby, such three-dimensional data as in one of FIGS. 10 to 13 is sampled.

A conversion table for linking results of the analysis in the present embodiment and the physical quantities in the external measuring apparatus is also stored within the surface roughness determination mechanism 123. The surface roughness determination mechanism 123 is designed so that the three-dimensional data obtained during analysis of any object to be measured can be checked against the registered table 122 and surface roughness can be output as results. In other words, it can be expressed that in the present embodiment, surface roughness is calculated using, for example, data equivalent to results of surface roughness measurement by an atomic force microscope. When surface roughness data is obtained, the foregoing sampling intervals ΔT will be shorter than, or desirably, sufficiently shorter than, those of the surface roughness predicted. This can be expressed as a sampling frequency desirably being higher than a frequency of the surface projections and depressions predicted.

During the determination of whether the data shown in one of FIGS. 5 to 8 relates to surface roughness, if the data is to be classified into surface roughness data and system noise data, the AFM-measured surface roughness information is not always necessary.

When a first threshold value, a second threshold value, and a third threshold value are provided for three axes shown in any one of FIGS. 10 to 13, determinations can be performed upon surface roughness data and system noise data and upon the surface roughness pitch and roughness.

Of course, if further information concerning the AFM-measured surface roughness information is available, even more highly accurate determinations can be performed since more practical roughness information exists.

Next, the detection of defects is described below.

Figure 9:
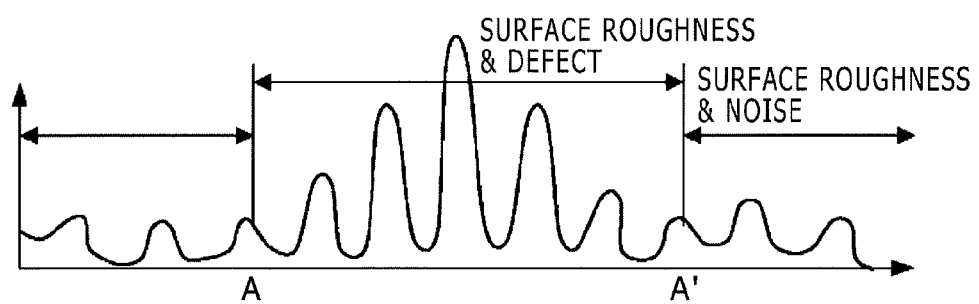
FIG. 9 shows a sampling signal waveform obtained from a defective sample.
Figure 14:
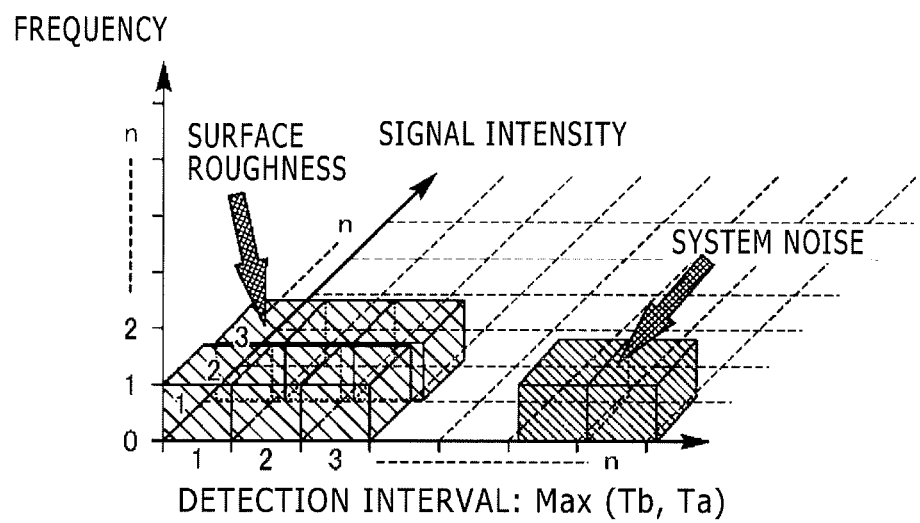
FIG. 14 shows a 3D graph that denotes a nondefective sample having surface roughness and causing system noise.
Figure 15:
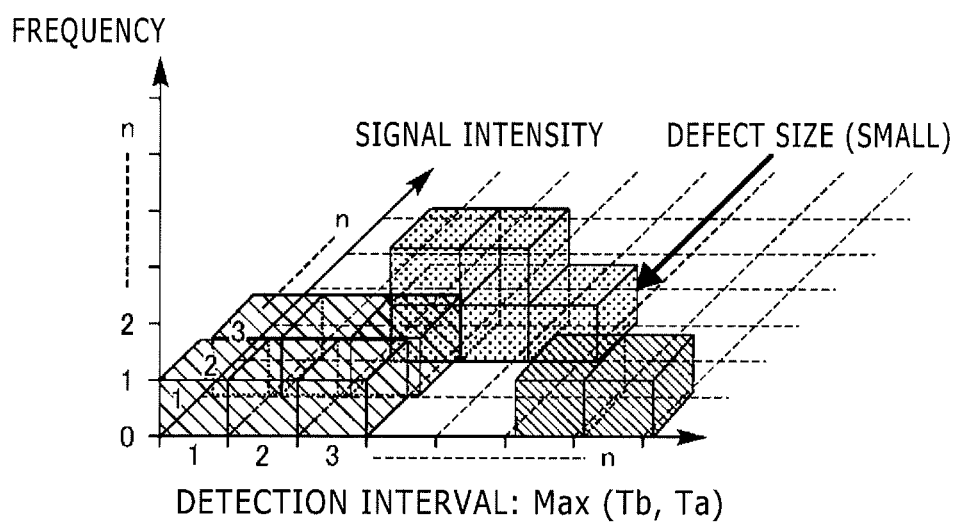
FIG. 15 shows a 3D graph that denotes a sample having relatively small defects.
Figure 16:
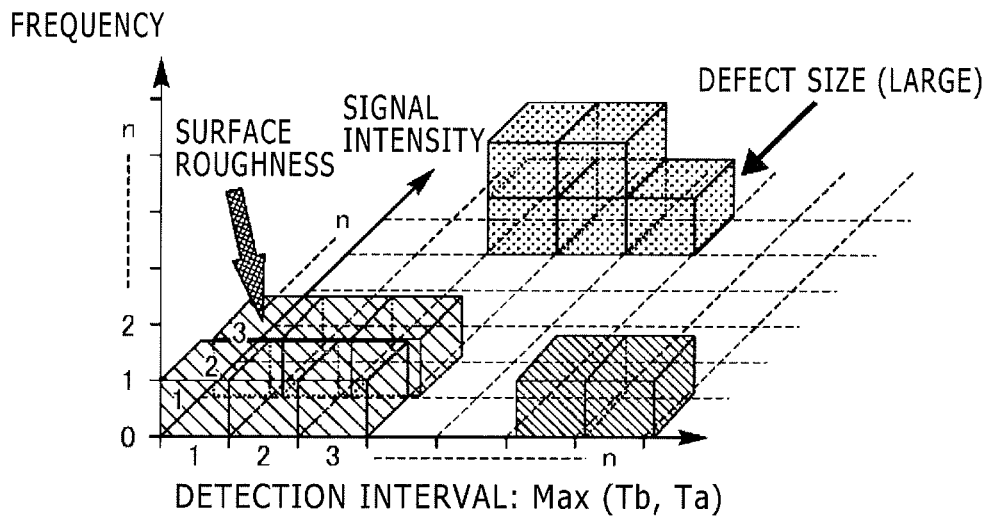
FIG. 16 shows a 3D graph that denotes a sample having relatively large defects.

Depending on whether a defect is present and on the dimensions of the defect, the detection signal as shown in FIG. 9 takes a pattern resembling that of any one of sets of three-dimensional data shown in FIGS. 14 to 16. If a defect is absent and only surface roughness or system noise is present, the detection signal takes a pattern resembling that of the data shown in FIG. 14. If a relatively small defect is present, such a pattern as in FIG. 15 appears, and if a relatively large defect is present, such a pattern as in FIG. 16 appears.

In this way, mapping on the three-dimensional data differs according to magnitude of the defect size. In addition, both surface roughness and system noise can be discriminated from each other on the three-dimensional data. The determination of surface roughness and system noise, the determination of the presence/absence of defects, and relative representation of defect dimensions can be achieved when a fourth threshold value, a fifth threshold value, and a sixth threshold value are provided for the three axes of the three-dimensional data.

In other words, it can be expressed that in the present embodiment, the above three-dimensional data can be used, for example, to determine at least one of whether surface roughness is present, whether system noise is present, and whether a defect is present. Conducting these determinations enables excellent defect detection over conventional inspection schemes. The first to sixth threshold values can be freely set and changed inside the inspection apparatus of the present embodiment.

(Second Embodiment)

Figure 17:
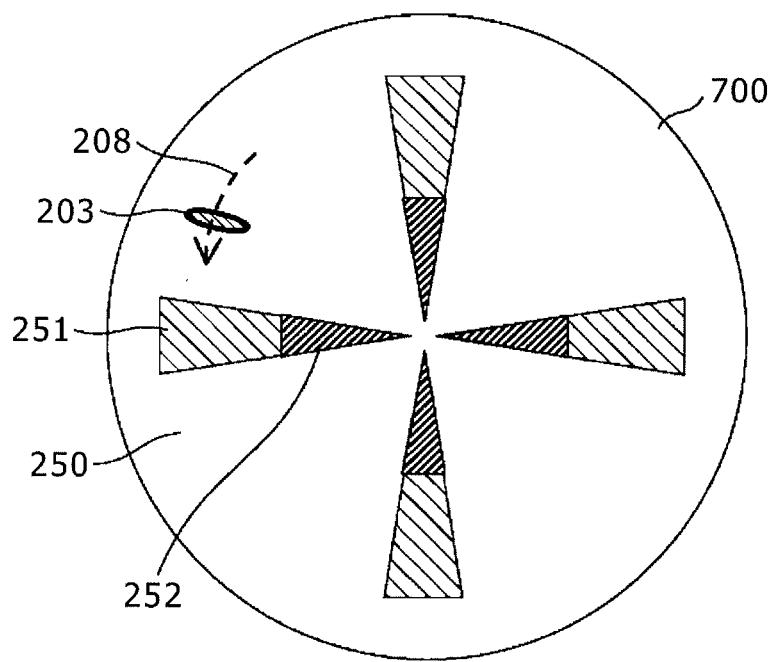
FIG. 17 is a diagram illustrating an example in which the roughness pitch and/or the amount of roughness varies from region to region on one surface under inspection.

Next, an inspection apparatus according to a second embodiment of the present invention is described below. The apparatus configuration is substantially the same as that of the first embodiment. Substantially the same elements as in the first embodiment are omitted and elements different from those of the first embodiment are mainly described. In an epitaxial wafer 700 (or a reclaimed wafer), even the same surface to be inspected may differ in roughness pitch and/or the amount of roughness, as shown in FIG. 17.

On a large portion of area, plane distributions in a radial direction and at inner and outer edges differ from those corresponding to the pattern 250 of FIG. 5. The radial section may exhibit the pattern 251 of FIG. 6 or the inner edge may exhibit the pattern 252 of FIG. 8. In order to gear up for such diversity of the surface to be inspected according to the present embodiment, the first to sixth threshold values described above are set and changed for each different region on the surface of the epitaxial wafer 700.

Based on the information relating to the rotating speed of the target object moving stage, the coordinate position in the scanning direction that is obtained from the coordinate detection means, and the size of the illumination spot, whether the region is a different one can be determined with the arithmetic unit 116, which is to say, the present embodiment can be expressed as, for example, varying inspection parameters according to region of the substrate.

For more accurate inspection, the AFM-measured surface roughness information described above and the conversion table may be provided for each different region on the surface of the epitaxial wafer 700. This will allow more accurate detection of defects even on a target surface whose state distribution is nonuniform, as of a reclaimed wafer.

(Third Embodiment)

Figure 18:
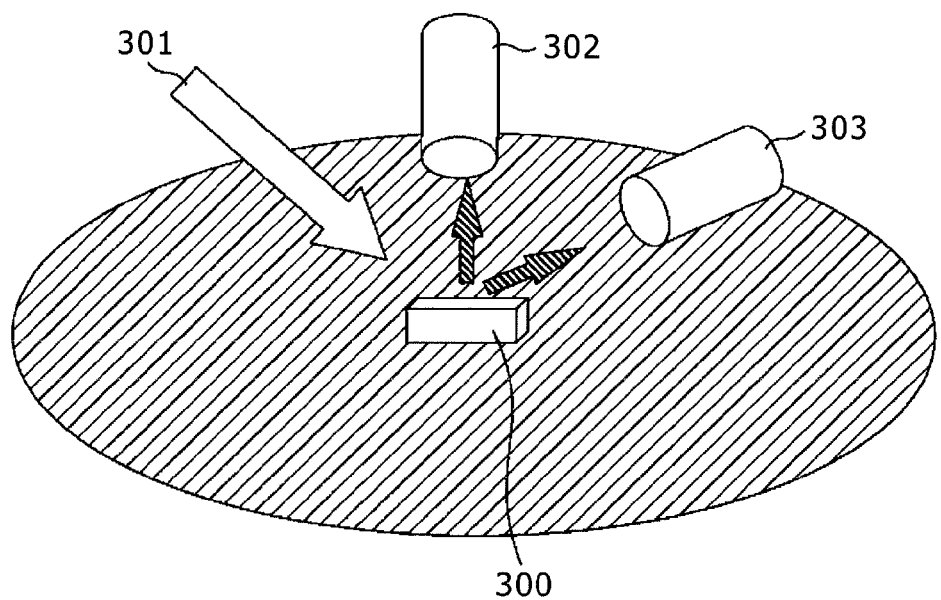
FIG. 18 is a diagram illustrating a third embodiment.

Next, a third embodiment is described below using FIGS. 18 to 20. A distribution of the light scattered from a defect depends on a shape and other factors of the defect, and appears as a pattern different for each of spatially arranged detectors. For example, if an oriented defect 300 is irradiated with illumination light 301 from such a direction as in FIG. 18, two different sets of three-dimensional data are obtained from a detector 302 placed directly above the oriented defect 300, and a detector 303 placed in a direction of a longer side of the oriented defect 300. The two sets of three-dimensional data appear as shown in FIGS. 19 and 20.

Figure 19:
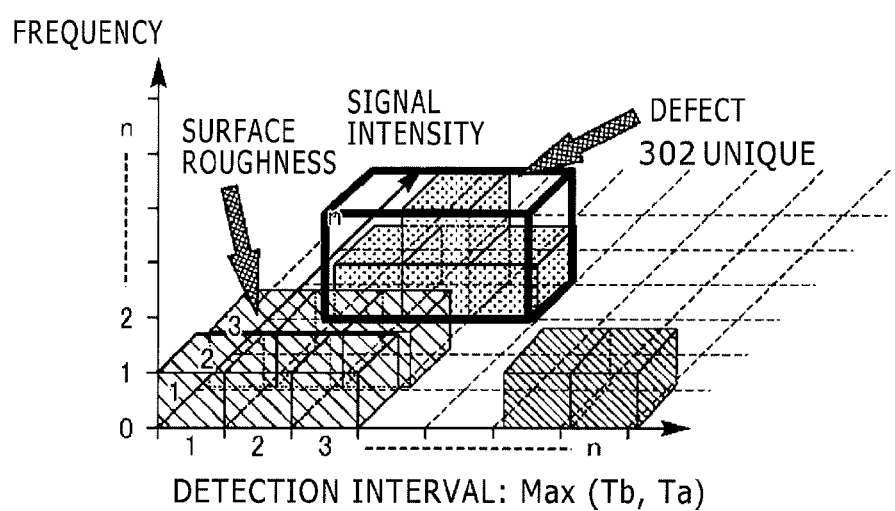
FIG. 19 shows a 3D graphic pattern obtained from a detector 302.
Figure 20:
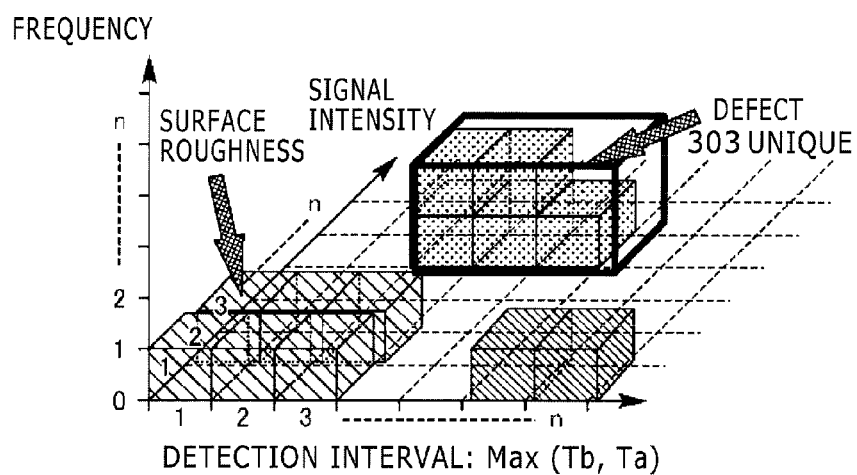
FIG. 20 shows a 3D graphic pattern obtained from a detector 303.

FIG. 19 shows a pattern corresponding to the detector 302, and FIG. 20 shows a pattern corresponding to the detector 303. Registering features of these patterns in advance and then accessing these registered features prior to and/or during measurement will allow highly accurate discrimination of an orientation property as well as shape of the detected defect.

(Fourth Embodiment)

Next, a fourth embodiment is described below. The fourth embodiment relates to obtaining more accurately a particle size that denotes surface roughness of a target object. There is a correlation between the particle size of the AFM-measured surface roughness and the intensity of scattered light. The fourth embodiment focuses upon this correlation. In the present embodiment, the particle size of the target object is acquired from both of data on an intensity ratio of a plurality of photodetectors and particle size data obtained from an AFM (or any other external apparatus if its scheme for measuring the particle size of surface roughness has higher data resolution than in optical inspection apparatuses), and intensity ratio data obtained from optical simulation. Thus, even more highly accurate data on more microscopic particle sizes can be obtained.

Figure 21:
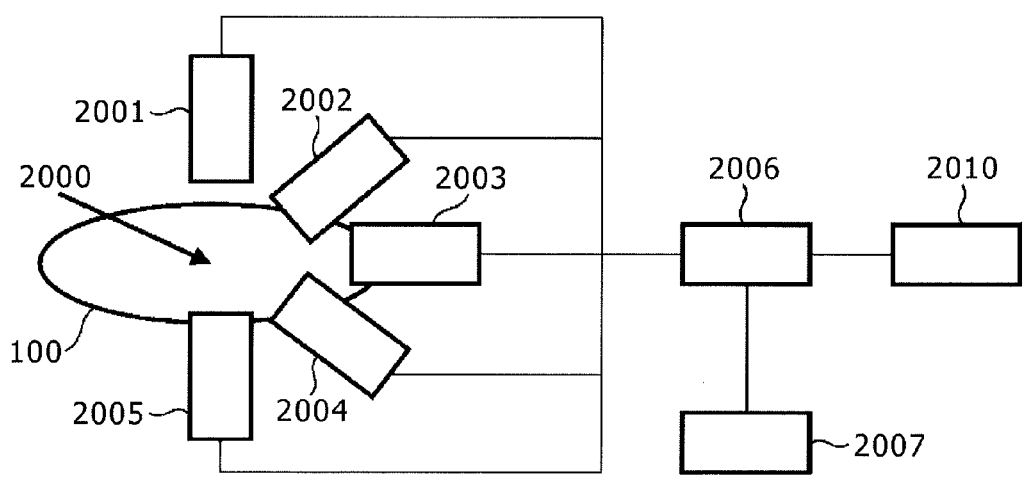
FIG. 21 is a diagram illustrating a fourth embodiment.

FIG. 21 is a diagram illustrating a fourth embodiment. In the fourth embodiment, a semiconductor wafer 100 is illuminated with illumination light 2000 from an oblique direction. Scattered light from the semiconductor wafer 100 is detected by photodetectors 2001 to 2005 that can respond at high speed. The photodetectors 2001 to 2005 here are arranged at different angles of elevation and orientation with respect to the wafer. Detection results by the photodetectors 2001 to 2005 are sent to a processing unit 2006.

The processing unit 2006 obtains three-dimensional data by conducting, with the method disclosed in the first embodiment, independent conversion based on signal luminance, detection intervals, and the frequency of detection, for each photodetector 2001 to 2005. Concurrently with the three-dimensional data conversion, the processing unit 2006 calculates the intensity ratios contained in the detection results of the photodetectors 2001 to 2005. This offers 3D intensity ratio data relating to the semiconductor wafer 100.

At least one of the following data is saved in a storage unit 2007:
(1) AFM-measured particle size data and a detector's ideal intensity ratio corresponding to the particle data
(2) A detector's ideal intensity ratio obtained by optical simulation, the intensity ratio corresponding to a particle size The processing unit 2006 reads out from the storage unit 2007 at least one of the two sets of data listed in items (1) and (2) above, and converts the intensity ratio within the detection results into the particle size that denotes surface roughness. Additionally in the present embodiment, the semiconductor wafer 100 is scanned over its entire surface and the above conversion is conducted, which then creates the particle size denoting the roughness of the entire surface of the semiconductor wafer 100. The processing unit 200 further uses the particle size obtained from the conversion, to determine surface roughness data from the three-dimensional data and conduct defect and system noise determinations as well. This allows the measurement of even more microscopic surface roughness, and defect determination.

(Fifth Embodiment)

Figure 24:
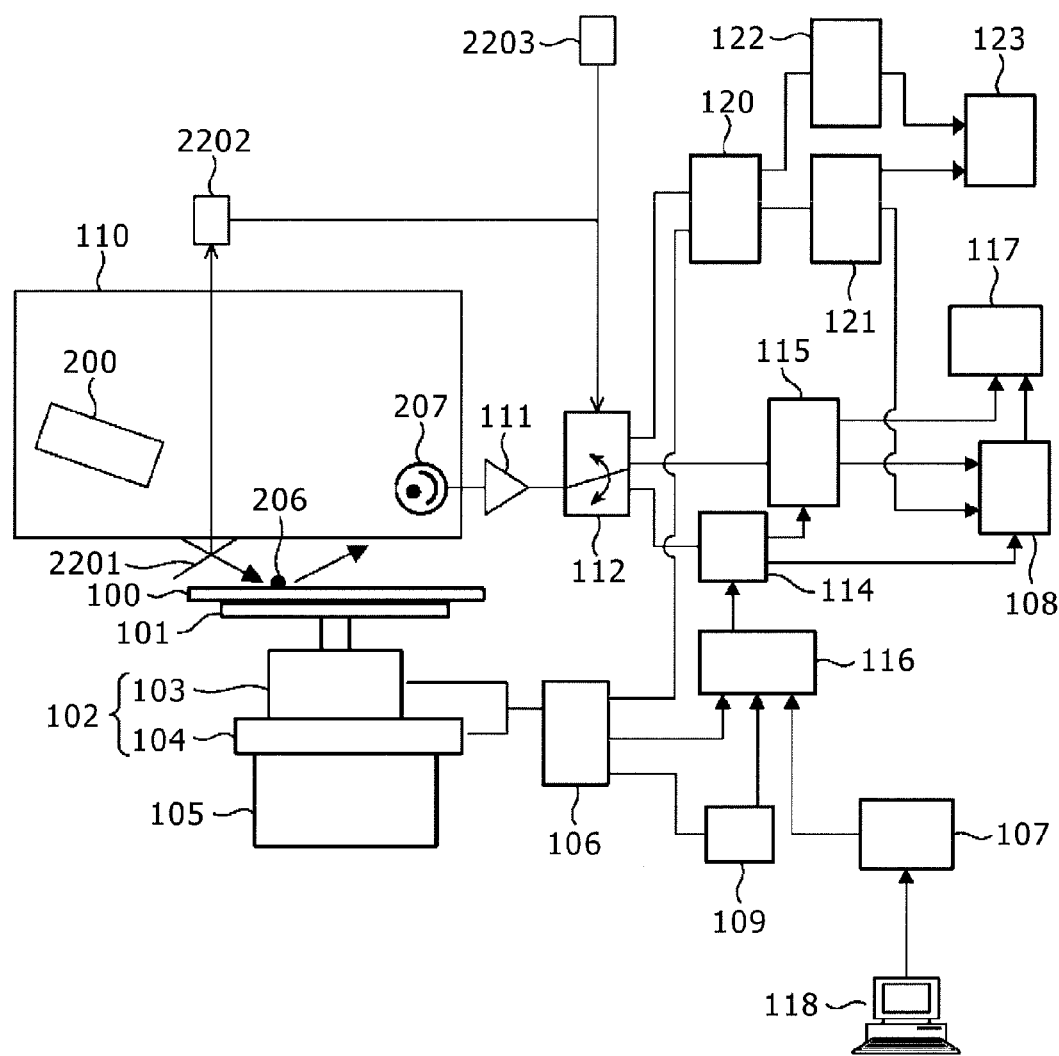
FIG. 24 is a diagram illustrating a fifth embodiment.

Next, a fifth embodiment is described below using FIG. 24. Elements different from those of the first embodiment are mainly described in the fifth embodiment. The fifth embodiment differs from the first embodiment in that illumination light for illuminating a semiconductor wafer 100 is pulse illumination light. On an optical path of the pulse illumination light, the fifth embodiment includes a branching unit 2201 that branches the pulse illumination light, and a photoelectric converter 2201 that converts the branched light into an electrical signal. The photoelectric converter 2201 generates the electrical signal only while the pulse illumination light is being emitted, so the electrical signal becomes a pulse signal. Furthermore, the fifth embodiment differs from the first embodiment in that the A/D converter 112 serves as a switching part of a gate circuit or the like, and performs switching by use of the electric signal from the photoelectric converter 2201. This means that whereas the sampling intervals ΔT in the first embodiment have depended upon the A/D converter 112, sampling intervals Δ in the fifth embodiment depend on emission intervals of the pulse illumination light. When surface roughness data is obtained, therefore, the emission intervals of the pulse illumination light in the present embodiment are shorter than, or desirably, sufficiently shorter than, intervals of the surface roughness predicted. This can be expressed as the emission intervals of the pulse illumination light desirably being higher than the frequency of the surface projections and depressions predicted.

By so doing, since sampling takes place only while the semiconductor wafer 100 is being illuminated with the pulse illumination light, impacts of background noise can be reduced and the surface shape analyzed and inspected with higher sensitivity. The time of day when the pulse illumination light is emitted may disagree with that at which the photoelectric converter 2201 generates the electrical signal, or time intervals at which the pulse illumination light is emitted may disagree with those at which the photoelectric converter 2201 generates the electrical signal. The present embodiment may further include a correction signal generator 2203 to generate a signal for correcting such a time lag.

DESCRIPTION OF REFERENCE NUMERALS

100 Semiconductor wafer
101 Chuck
102 Target object moving stage
103 Rotating stage
104 Translating stage
105 Z-stage
106 Inspection coordinate detection mechanism
107 Host CPU
108 Foreign substance/defect determination mechanism
109 Foreign substance/defect detection mechanism
110 Illumination and detection optical system
111 Amplifier
112 A/D converter
114 Variable filter
115 Subtractor
116 Arithmetic unit
117 Particle size calculation mechanism
118 Input means
120 Measured-data memory 121 3D analyzing mechanism
122 Table
123 Surface roughness determination mechanism
200 Light source
201 Emitted beam
202 Irradiation lens
203 Illumination spot
204 Width in a direction of major axis
205 Width in a direction of minor axis
206 Foreign substance/defect
207 Photodetector
208 θ-scan
209 Expander
210 Converging lens
220 Sampling intervals ΔT
221 ΔSout
250 Pattern of FIG. 5
251 Pattern of FIG. 6
252 Pattern of FIG. 8
300 Oriented defect
301 Illumination light
302, 303 Detectors

The invention claimed is:

1. A measuring apparatus for measuring data on a shape of a substrate surface, the apparatus comprising:
an irradiating unit that irradiates the substrate with light;
a detecting unit that detects the light scattered from the substrate;
a sampling unit that samples detection results of the detecting unit at a specific frequency; and
a processing unit, adapted to:
convert sampling results of the sampling unit into three-dimensional data based upon signal intensity, detection intervals, and a frequency of detection that correspond to the detection results; and
obtain the shape of the substrate by use of results of the three-dimensional data conversion.

2. The measuring apparatus according to claim 1, wherein the processing unit uses the three-dimensional data conversion results to determine at least one of whether surface roughness exists, whether system noise exists, and whether a defect exists.

3. The measuring apparatus according to claim 1, wherein surface roughness is calculated using data equivalent to results of surface roughness measurement with an atomic force microscope.

4. The measuring apparatus according to claim 1, wherein the processing unit varies inspection parameters according to region of the substrate.

* * * * *